(12) United States Patent
Smith et al.

(10) Patent No.: US 7,879,870 B2
(45) Date of Patent: Feb. 1, 2011

(54) TREATMENT OF INFLAMMATORY AND ULCERATIVE DISEASES OF THE BOWEL WITH OPIOID ANTAGONISTS

(76) Inventors: Jill P. Smith, 129 N. 30th St., Camp Hill, PA (US) 17011; Ian S. Zagon, 589 Cook Ct., Hummelstown, PA (US) 17036; Moshe Rogosnitzky, P. O. Box 386, Telz Stone, IL (US) 90840

( * ) Notice: Subject to any disclaimer, the term of this patent is extended or adjusted under 35 U.S.C. 154(b) by 344 days.

(21) Appl. No.: 11/735,548

(22) Filed: Apr. 16, 2007

(65) Prior Publication Data

US 2008/0015211 A1 Jan. 17, 2008

Related U.S. Application Data

(60) Provisional application No. 60/745,119, filed on Apr. 19, 2006.

(51) Int. Cl.
*A61K 31/485* (2006.01)
(52) U.S. Cl. ..................................... 514/282
(58) Field of Classification Search ........................ None
See application file for complete search history.

(56) References Cited

U.S. PATENT DOCUMENTS

| | | | |
|---|---|---|---|
| 4,987,136 A | 1/1991 | Kreek et al. |
| 4,994,466 A | 2/1991 | Sherman et al. |
| 5,013,739 A | 5/1991 | Bihari et al. |
| 5,631,263 A | 5/1997 | Portoghese et al. |
| 6,194,382 B1 | 2/2001 | Crain et al. |
| 6,395,705 B2 | 5/2002 | Crain et al. |
| 6,458,795 B1 | 10/2002 | Bergeron, Jr. |
| 6,664,270 B2 | 12/2003 | Bergeron, Jr. |
| 6,734,188 B1 | 5/2004 | Rhodes et al. |
| 6,737,400 B2 | 5/2004 | Crain et al. |
| 6,818,656 B2 | 11/2004 | Bergeron, Jr. |
| 7,157,462 B2 | 1/2007 | Sun et al. |
| 2005/0261329 A1 | 11/2005 | Wu et al. |

OTHER PUBLICATIONS

International Search Report for PCT/US2007/009228, mailed Jun. 3, 2008.
www.lowdosenaltrexone.com, as accessed on Mar. 21, 2007.
Smith et al., "Low-Dose Naltrexone Therapy Improves Active Crohn's Disease," Am. J. Gastroenterol. 102, 1-9 (2007).
Penn State College of Medicine News Release, "Penn State Research Shows Withdrawal Drug Offers Symptom Relief to Crohn's Sufferers" (May 23, 2006).
"LDN—Low Dose Naltrexone," www.digitalnaturopath.com (as accessed on Apr. 17, 2007).
"Low Dose Naltrexone: Informal Clinical Study Report, Jul. 1, 2005", www.stronadzieci.org (as accessed on Apr. 17, 2007).

*Primary Examiner*—Phyllis G. Spivack
(74) *Attorney, Agent, or Firm*—Laurence Weinberger

(57) ABSTRACT

Methods for the treatment of inflammatory and ulcerative diseases of the bowel (e.g., Crohn's disease and ulcerative colitis) with a therapeutically effective dose less than 50 mg. of opioid antagonists (e.g., naltrexone, nalmefene or naloxone) are disclosed. An embodiment of the invention includes a method of pharmaceutical treatment comprising orally administering to a human subject having Crohn's disease or ulcerative colitis a therapeutic pharmaceutical composition once per day in the evening or at bedtime, wherein the pharmaceutical composition comprises form about 3 mg to about 4.5 mg of naltrexone, nalmefene, naloxone, or a hydrochloride salt thereof in an immediate release solid dosage formulation.

20 Claims, 10 Drawing Sheets

TREATMENT OF INFLAMMATORY AND ULCERATIVE DISEASES OF THE BOWEL WITH OPIOID ANTAGONISTS

CROSS REFERENCE TO RELATED APPLICATIONS

This application claims the priority of U.S. provisional patent application No. 60/745,119, filed on Apr. 19, 2006, incorporated herein by reference in its entirety.

FIELD

Example embodiments of the invention include methods for the treatment of inflammatory and ulcerative diseases of the bowel (e.g., Crohn's disease and ulcerative colitis) with low dose opioid antagonists (e.g., naltrexone, nalmefene or naloxone), pharmaceutical compositions for use in such methods, and methods for the manufacture of such pharmaceutical compositions.

BACKGROUND

Chronic relapsing and remitting inflammation of the gastrointestinal tract are hallmarks of ulcerative colitis and Crohn's disease, conditions termed inflammatory bowel diseases ("IBD"). The peak age of onset of this disease is between the first and fourth decades of life, with a prevalence of 100-200 per 100,000 in Europe and North America. Inflammatory bowel disease accounts for significant morbidity and decreased quality of life, and is responsible for nearly US$2.0 billion in annual medical costs in the United States. Although there has been progress in defining the pathogenesis of these diseases, their cause remains obscure. The current most comprehensive hypothesis is that IBD is a heterogeneous group of diseases that have a final manifestation, which is mucosal inflammation, and that several genetic and environmental factors are implicated in the pathogenesis of the disease.

Because of the name, IBD is often confused with irritable bowel syndrome ("IBS"), a troublesome but much less serious condition. Irritable bowel syndrome is a gastrointestinal disorder characterized by altered bowel habits and abdominal pain in the absence of detectable structural abnormalities, such as inflammation or ulceration. Irritable bowel syndrome is not an inflammatory disease and it is not characterized by ulceration of the bowel. No clear diagnostic markers exist and no pathognomonic abnormalities have been identified for IBS, so all definitions of the disease are based on the clinical presentation. Until recently, many physicians did not consider IBS to be a disease at all; they viewed it as nothing more than a somatic manifestation of psychological stress. Typical chemotherapies for IBS include stool bulking agents, antispasmodics, and antidiarrheal agents.

In contrast, Crohn's disease is an inflammatory disease characterized by transmural, patchy, granulomatous inflammation of any part of the gastrointestinal tract, although it is common in the ileocecal area. Symptoms of Crohn's disease include abdominal pain, diarrhea, gastrointestinal bleeding, malabsorption, and weight loss. Although the etiology is unknown, research suggests it involves a complex interplay of environmental, genetic, microbial, immune, and nonimmune factors. Biopsies obtained from the bowel in subjects with Crohn's disease reveal inflammatory cells suggesting that the bowel is either reacting immunologically to a stimulus or the endogenous immune system of the gastrointestinal track is off balance.

Treatment of Crohn's disease usually includes administration of anti-inflammatory drugs, including compounds designed to reduce the inflammatory response, such as corticosteroids, cyclosporine, and azathioprine, which often lead to serious side effects. Major advances in the understanding of the pathogenesis of IBD have led to the development of novel immunotherapies. Such treatments include the administration of chimeric monoclonal antibodies specific for molecules expressed by the T-cells population or antibodies specific for cytokines known to be central to the pathogenesis of mucosal inflammation (anti-tumor necrosis factor, TNF). Although this specific immunotherapy has helped those with Crohn's disease, still about 20% do not respond to this treatment and many cannot continue this therapy due to untoward side effects. Additionally, treatment with the monoclonal antibody infliximab (sold as REMICADE®, a registered trademark of Centocor, Inc. of Malvern, Pa.) is expensive with each infusion costing in excess of US$3,000.

Ulcerative colitis is a form of colitis, an inflammatory disease of the intestine, usually the colon, that includes characteristic ulcers. Symptoms of active disease usually include diarrhea mixed with blood, usually accompanied with varying degrees of abdominal pain, from mild discomfort to severely painful cramps. Although ulcerative colitis has no known cause, there is a presumed genetic component to susceptibility. The disease may be triggered in a susceptible person by environmental factors. Although dietary modification may reduce the discomfort of a person with the disease, ulcerative colitis is not thought to be caused by dietary factors. As with Crohn's disease, treatment includes administration of anti-inflammatory drugs, immunosuppression, and biological therapy targeting specific components of the immune response.

When anti-inflammatory therapies fail, colectomy is occasionally necessary, which is considered to be curative for ulcerative colitis. Surgery is generally reserved for complications of Crohn's disease or when disease that resists treatment with drugs is confined to one location that can be removed. Surgery is also used to manage complications of Crohn's disease, such as fistulae and small bowel obstructions, and for resection and anastomosis (e.g., ileocolonic resection). Surgery rarely cures Crohn's disease, and recurrence often reappears in previously unaffected areas of the intestine.

Accordingly, a continuing need exists for effective pharmacological treatments of inflammatory bowel disease, such as Crohn's disease and ulcerative colitis.

SUMMARY

Example embodiments of the invention include methods for the treatment of inflammatory and ulcerative diseases of the bowel (e.g., Crohn's disease and ulcerative colitis) with low dose opioid antagonists (e.g., naltrexone, nalmefene or naloxone), pharmaceutical compositions for use in such methods, and methods for the manufacture of such pharmaceutical compositions.

In another example embodiment, the invention includes the use of an opioid antagonist in the preparation of a low dose pharmaceutical composition for the treatment of a bowel disease characterized by inflammation or ulceration of the intestinal wall.

In yet another embodiment, the invention includes a method for treating a bowel disease comprising administering to a subject in need thereof a low dose of an opioid antagonist effective to treat a bowel disease in the subject (e.g., a human), wherein the bowel disease is characterized by inflammation or ulceration of the intestinal wall.

In still yet another embodiment, the invention includes a pharmaceutical composition for use in the treatment of a bowel disease characterized by inflammation or ulceration of the intestinal wall, the pharmaceutical composition comprising a low dose (e.g., less than about 5 mg) of an opioid antagonist.

The invention provides heretofore unknown evidence that low dose naltrexone, an opioid antagonist, is a safe and effective treatment for Crohn's disease. In summary, an open-labeled prospective trial of human subjects was conducted, as described more fully herein below. The safety and efficacy of low dose naltrexone ("LDN") was tested in patients with active Crohn's disease. Eligible subjects with histologically and endoscopically confirmed active Crohn's having a Crohn's Disease Activity Index ("CDAI") score of 220-450 were enrolled in a study using 4.5 mg naltrexone/day. Infliximab was not allowed for a minimum of eight weeks prior to study initiation or while in the study. Other therapy for Crohn's disease that was at a stable dose for four weeks prior to enrollment was continued at the same doses. Patients completed the Inflammatory Bowel Disease Questionnaire ("IBDQ") and the Short-Form ("SF-36") quality of life surveys and CDAI scores were assessed pretreatment, every four weeks on therapy, and four weeks after completion of the study drug. LDN was administered by mouth each evening for a twelve-week period. Seventeen patients with a mean CDAI score of 356±27 were enrolled. CDAI scores decreased significantly ($p=0.01$) with LDN, and remained lower than baseline four weeks after completing therapy. Eighty-nine percent of patients exhibited a response to therapy and 67% achieved a remission ($p<0.001$). Improvement was recorded in both quality of life surveys with LDN compared to baseline. No laboratory abnormalities were noted.

The invention also provides heretofore unknown evidence that the opioid antagonist naltrexone reduces inflammation of the bowel in a chemically-induced mouse model of ulcerative colitis, as described more completely herein below. Briefly, laboratory mice received either untreated drinking water or water containing 2% dextran sulfate sodium ("DSS") for six days. Three days after DSS introduction, animals were administered 0.1 mL saline (control) or naltrexone ("NTX", 6.3 or 350 µg/kg) daily for six days. Disease activity index ("DAI") scores were calculated daily. Mice were necropsied on day nine and colon inflammation was analyzed histologically. Colonic RNA was evaluated by microarray and real-time RT-PCR. By day 4, DSS-treated animals had significant weight loss ($p=0.006$) and higher DAI scores ($p<0.001$) compared to water controls. DSS-treated mice that received naltrexone (350 µg/kg) had less weight loss, lower DAI scores, and less inflammation compared to DSS mice treated with saline. RNA encoding pro-inflammatory cytokines IL-6 and IL-12 was significantly elevated in DSS-treated mice, and after naltrexone treatment these cytokine RNAs were decreased to levels near or equal to that in mice without colitis. Expression of the transcription factors STAT3 and STAT4, downstream effectors of cytokine signaling, was also up-regulated in DSS-treated mice and similarly reversed by naltrexone. Naltrexone therefore appears to have reversed disease manifestations and histologic evidence of inflammation in DSS-induced colitis.

Other features and advantages of the present invention will be apparent from the following more detailed description of preferred embodiments, taken in conjunction with the accompanying drawings that illustrate, by way of example, principles of the invention.

DETAILED DESCRIPTION

Figure 1:
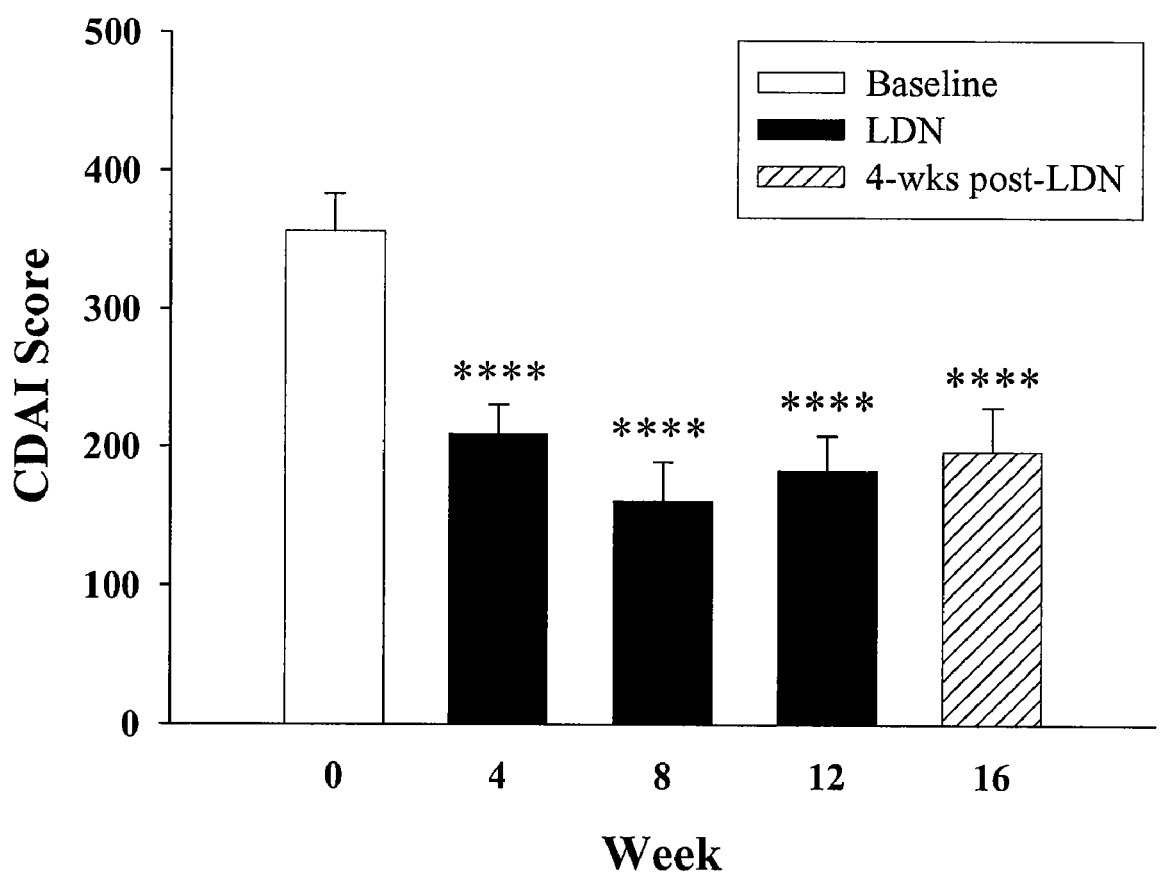
FIG. 1 illustrates mean Crohn's Disease Activity Index scores associated with LDN therapy in human patients.

Example embodiments of the invention include methods for the treatment of inflammatory and ulcerative diseases of the bowel with low dose opioid antagonists (e.g., less than about 5 mg naltrexone, nalmefene or naloxone per day), pharmaceutical compositions for use in such methods, and methods for the manufacture of such pharmaceutical compositions.

In an embodiment, the invention relates to the treatment of "inflammatory bowel disease," such as Crohn's disease and ulcerative colitis. Inflammatory bowel disease ("IBD") is a group of inflammatory conditions of the large intestine and the small intestine. Although similar in name, it should not be confused with irritable bowel syndrome ("IBS"), which is a different condition having a different pathology and different symptoms. Principal forms of IBD are Crohn's disease and ulcerative colitis ("UC"), although other forms include collagenous colitis, lymphocytic colitis, ischemic colitis, diversion colitis, Behçet's syndrome, infective colitis, and indeterminate colitis. Crohn's disease and UC differ is the location and nature of the inflammatory changes in the intestine. Crohn's may affect any part of the gastrointestinal tract, from mouth to anus, although the terminal ileum is the area most commonly involved. Ulcerative colitis, in contrast, is generally restricted to the colon and the rectum. Microscopically, ulcerative colitis is restricted to the mucosa (i.e., the epithelial lining), while Crohn's disease may affect the entire thickness of the intestinal wall. Finally, Crohn's disease and ulcerative colitis present with extra-intestinal manifestations such as liver problems, arthritis, skin manifestations and eye problems.

Inflammatory bowel disease may present with any of the following symptoms: abdominal pain or discomfort, abnormal bowel movement frequency (e.g., diarrhea), intestinal stenosis or fistulization, perianal discomfort or pruritus, vomiting, hematochezia (i.e., bloody stool), weight loss and various associated complaints or diseases. IBD may also present with various fistulae, including one or more gastrocolic fistulae, gastrojejunocolic fistulae, enterocutaneous fistulae, anorectal fistulae, enterovaginal fistulae, enterovesical fistulae, and enteroenteral fistulae. Diagnosis of inflammatory bowel disease is generally by colonoscopy with biopsy of pathological lesions or by radiographic (e.g., X-ray) examination, which often reveals inflammation or ulceration of the ileum or colon (e.g., the ileocecum).

Accordingly, an embodiment of the invention includes a method for treating a bowel disease comprising administering to a subject in need thereof a low dose of an opioid antagonist effective to treat a bowel disease in a subject (e.g., a human patient), wherein the bowel disease is characterized by inflammation or ulceration of the intestinal wall or any portion thereof, e.g. the mucosa.

As used herein a "bowel disease" may be characterized by abdominal pain or discomfort, abnormal bowel movement frequency, intestinal stenosis or fistulization, perianal discomfort or pruritus, or abnormal stool consistency. Furthermore, a "bowel disease" may be characterized by inflammation or ulceration of the small intestine (e.g., the ileum) or colon (e.g., the ileocecum). A "bowel disease" may also be characterized by the presence of a fistula, e.g. of the gastrointestinal system. In particular, a "bowel disease" may include "inflammatory bowel disease" (IBD), such as Crohn's disease or ulcerative colitis. A "bowel disease" as used herein does not include irritable bowel syndrome per se.

Another embodiment of the invention includes the use of an opioid antagonist in the preparation of a low dose pharmaceutical composition for the treatment of a bowel disease (e.g., IBD) characterized by inflammation or ulceration of the intestinal wall or any portion thereof, e.g. the mucosa.

In still yet another embodiment, the invention relates to a pharmaceutical composition for use in the treatment of a bowel disease characterized by inflammation or ulceration of the intestinal wall or any portion thereof, e.g. the mucosa, the pharmaceutical comprising a low dose of an opioid antagonist.

In still another embodiment, the invention relates to a pharmaceutical composition for use in the treatment of a fistula, e.g. a connection from the bowel to either the skin, another part of the bowel, the bladder, or vagina, the pharmaceutical comprising a low dose of an opioid antagonist. The fistula may be incident, to or associated with, a bowel disease characterized by inflammation or ulceration of the intestinal wall or any portion thereof, e.g. the mucosa.

In another embodiment, the invention includes a method for treating a bowel disease comprising administering to a subject in need thereof a pharmaceutical composition comprising a low dose of an opioid antagonist effective to treat a bowel disease in said subject, wherein said bowel disease is characterized by inflammation or ulceration of the intestinal wall. The amount of opioid antagonist may be from about 1.75 mg to about 4.5 mg per dose, or alternatively form about 1.75 mg to about 3 mg per dose, or in another embodiment from about 3 mg to about 4.5 mg per dose.

As used herein, an "opioid antagonist" may be selected from the group consisting of naltrexone, nalmefene, naloxone, metabolites thereof having opioid antagonist activity, pharmaceutically acceptable salts thereof, prodrugs thereof, and combinations thereof. For example, an opioid antagonist may be naltrexone, nalmefene, naloxone, or a hydrochloride salt thereof (e.g., naltrexone hydrochloride, nalmefene hydrochloride, and naloxone hydrochloride).

According to an embodiment of the invention, the opioid antagonist is administered as a "low dose." For example, the low dose of the opioid antagonist may be from about 1.75 mg to about 4.5 mg, or alternatively form about 1.75 mg to about 3 mg, or in another embodiment from about 3 mg to about 4.5 mg. The low dose of opioid antagonist may be administered once per day, e.g. in the evening or at bedtime so that $t_{max}$ occurs shortly after sleep commences. Accordingly, in an embodiment, the opioid antagonist is provided as a pharmaceutical composition, which may be administered once per day in the evening or at bedtime. In another embodiment, the pharmaceutical composition is administered once per day in the morning or after waking from sleep.

Another embodiment of the invention includes a method of pharmaceutical treatment comprising orally administering to a human subject having Crohn's disease or ulcerative colitis a therapeutic pharmaceutical composition once per day in the evening or at bedtime (or once per day in the morning or after waking from sleep), wherein the pharmaceutical composition comprises form about 3 mg to about 4.5 mg of naltrexone, nalmefene, naloxone, or a hydrochloride salt thereof per dose, which may be an immediate release solid dosage formulation.

The invention also relates to pharmaceutical compositions and the preparation thereof. The pharmaceutical composition may be formulated as a solid dosage form suitable for oral administration. Furthermore, the solid dosage form may be an immediate release formulation comprising an opioid antagonist and an excipient, which may be selected from, e.g. the group consisting of sucrose, cellulose, and combinations thereof. In another embodiment, the low dose pharmaceutical composition may be formulated as a liquid dosage form suitable for oral administration. For example, the liquid dosage form may comprise an opioid antagonist and a liquid carrier, which may comprise water. Similarly, the pharmaceutical composition may be formulated as a topical dosage form suitable for topical administration.

It is especially advantageous to formulate pharmaceutical compositions in unit dosage form for ease of administration and uniformity of dosage. A unit dosage form refers to physically discrete units suited as unitary dosages for the subjects to be treated; each unit containing a predetermined quantity of opioid antagonist calculated to produce the desired therapeutic effect in association with the required pharmaceutical vehicle. The specification of unit dosage forms may be dictated by and directly dependent on the unique characteristics of the particular opioid antagonist and the limitations inherent in the art of compounding such a compound for the treatment of a bowel disease.

Opioid antagonists may be formulated for administration using physiologically acceptable carriers or excipients in a manner fully within the skill of the art. For example, the opioid antagonists, optionally with the addition of pharmaceutically acceptable excipients, may be suspended or dissolved in an aqueous medium, with the resulting solution or suspension then being sterilized. An opioid antagonist may be orally administered, for example, with an inert diluent or an edible carrier. The opioid antagonist and other ingredients may also be enclosed in a hard or soft shell gelatin capsule or compressed into tablets. For oral therapeutic administration, the opioid antagonist may be incorporated with excipients and used in the form of ingestible tablets, buccal tablets, troches, capsules, elixirs, suspensions, syrups, wafers, and the like.

For topical administration, the opioid antagonist may be provided in the form of ointments, creams, gels, lotions, shampoos, powders (including spray powders), pessaries, tampons, sprays, dips, aerosols, or drops (e.g., eye ear or nose drops). The opioid antagonist may also be provided in the form of a transdermal or percutaneous drug delivery system, e.g. a transdermal patch.

The percentage of the opioid antagonist in the pharmaceutical compositions may, of course, be varied. The relative amount of the opioid antagonist in such therapeutically useful compositions is such that a suitable dosage will be obtained. Furthermore, the pharmaceutical composition may be formulated as an immediate release formulation (preferred), an intermediate release formulation, or an extended release formulation according to methods well known in the art.

Opioid antagonists are typically alkaloids that contain a basic functional group, such as amino group, and are thus capable of forming pharmaceutically acceptable salts with pharmaceutically acceptable acids. The term "pharmaceutically acceptable salts" in this respect, refers to the relatively non-toxic, inorganic and organic acid addition salts of opioid antagonists. These salts may be prepared in situ during the final isolation and purification of the compounds, or by separately reacting a purified compound in its free base form with a suitable organic or inorganic acid, and isolating the salt thus formed. Representative salts include the hydrohalide (including hydrobromide and hydrochloride), sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, 2-hydroxyethylsulfonate, laurylsulphonate salts and the like. See, e.g. Berge, et al., "Pharmaceutical Salts", *J. Pharm. Sci.* 66, 1-19 (1977).

In other cases, an opioid antagonist may contain one or more acidic functional groups and thus be capable of forming pharmaceutically acceptable salts with pharmaceutically acceptable bases. The term "pharmaceutically acceptable salts" in these instances refers to the relatively non-toxic, inorganic and organic base addition salts of opioid antagonists. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. See, Berge, Ibid.

"Pharmaceutically acceptable" includes those compounds, materials, compositions, or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The invention also pertains to prodrugs of opioid antagonists. Prodrugs are compounds that are converted in vivo to active forms. Prodrugs can be used to alter the biodistribution or the pharmacokinetics of a particular compound. For example, a carboxylic acid group can be esterified, e.g. with a methyl group or an ethyl group to yield an ester. When the ester is administered to a subject, the ester is cleaved, enzymatically or non-enzymatically, reductively, oxidatively, or hydrolytically, to reveal the anionic group. An anionic group may be esterified with moieties (e.g., acyloxymethyl esters) that may be cleaved to reveal an intermediate compound that subsequently decomposes to yield the active compound. The prodrug moieties may be metabolized in vivo by esterases or by other mechanisms to carboxylic acids. Examples of prodrugs and their uses are well known in the art. Prodrugs of opioid antagonists may be prepared in situ during their final isolation and purification or by separately reacting the purified compound in its free acid or base form with a suitable derivatizing agent. See, e.g. R. B. Silverman, "The Organic Chemistry of Drug Design and Drug Action," Academic Press, Chp. 8 (1992).

EXAMPLES

Crohn's Disease

In the following detailed example, low dose naltrexone, an opioid antagonist, is shown to be a safe and effective treatment for Crohn's disease. In a human clinical experiment, eligible patients were both male and female, at least eighteen years of age, and with the confirmed diagnosis of Crohn's disease by either endocopic or radiographic procedures. Patients had moderate to severely active disease as defined by a Crohn's Disease Activity Index (CDAI score) of >220 and <450. See, Best, et al., "Development of a Crohn's disease activity index. National Cooperative Crohn's Disease Study," *Gastroenterology* 70, 439-44 (1976). Patients taking stable doses of aminosalicylates, immunomodulators, corticosteroids, or antibiotics were permitted to enter the study, and they were continued at the same dosage throughout the trial. Women of childbearing age were permitted to enroll and, if not surgically sterile, were required to use adequate contraception (defined as oral or depot contraceptive, IUD, or barrier plus spermicide) for the duration of the study. These women were required to continue adequate contraception for three months after the completion of the study. Exclusion criteria included women who were pregnant or breastfeeding, subjects with an ileostomy, colostomy, ileorectal anastomosis, or short bowel syndrome from surgery, and patients with abnormal liver function tests. Subjects taking tacrolimus, cyclosporine, mycophenolate, or infliximab within eight weeks of enrollment were excluded.

TABLE 1

| Patient Demographics | |
|---|---|
| Mean age ± SEM (years) | 42.1 ± 2.6 |
| (range) | (23-63) |
| Gender, N (% of patients) | |
| Male | 3 (18%) |
| Female | 14 (82%) |
| Mean body weight ± SEM (kg) | 72 ± 4 |
| (range) | (53-101) |
| Disease site | |
| Small bowel | 2 (12%) |
| Small bowel & colon | 10 (59%) |
| Colon | 5 (29%) |
| Past resection performed, N (% of patients) | 8 (47%) |
| Prior anti-TNF-α therapy, n (% of patients) | 13 (76%) |
| Concomitant meds for Crohn's, N (% of patients) | |
| Aminosalicylates | 11 (65%) |
| Immunomodulators | 8 (47%) |
| Glucocorticoids | 4 (24%) |
| Antibiotics | 1 (6%) |

The study was an open-labeled pilot investigation to evaluate safety, toxicity, and response to LDN in subjects with active Crohn's disease. Eligibility was assessed by telephone, and potential candidates were scheduled for a screening visit. At the screening visit, patients were subjected to a history and physical examination and laboratory testing (chemistry panel, complete blood count ["CBC"], urinalysis, and erythrocyte sedimentation rate ["ESR"]). Patients were dispensed a seven-day diary to record symptoms of frequency of diarrhea, abdominal pain, and general well-being. Within fourteen days, patients returned for assessment and calculation of the CDAI score. Qualifying subjects were dispensed medication and given a new diary in order to calculate the subsequent month's CDAI score at the conclusion of this visit (baseline). Patients returned after two weeks for an interim visit to evaluate side effects and perform a CBC. Follow-up visits were scheduled for weeks 4, 8, 12, and 16.

Naltrexone hydrochloride was compounded into capsules containing 4.5 mg by GMP-approved standards at a pharmacy. Because the dosage used in this study was lower than the current FDA-approved dose of 50 mg, it is referred to as "low dose naltrexone" or LDN. Quality assurance of packaging and purity were confirmed an analytical research laboratory. Patients were treated with LDN orally each evening for three months. A monthly supply of medication was dispensed to patients. On the first visit, an additional ten-day supply of LDN was provided in the event of an appointment delay. Subjects were required to bring the vials to each appointment for counting and drug accountability; extra capsules were returned on the day of the visit and another month's supply dispensed.

Routine blood work including CBC, chemistry panel, and ESR were assessed monthly. In addition, urine tests and pregnancy tests were done for monitoring and safety purposes pretreatment and at each monthly visit. C-reactive protein ("C-RP") was measured at baseline and at week 12. [Met$^5$]-enkephalin levels were determined by radioimmunoassay ("RIA") at baseline and weeks 4, 8, 12, and 16.

In order to assess the effect of LDN on disease activity, patients kept a Crohn's symptom diary for the seven days preceding each visit for calculation of the CDAI score. To assess quality of life, patients completed two standardized quality of life surveys, the Inflammatory Bowel Disease Questionnaire ("IBDQ") and SF-36 Health Survey. See, Irvine, et al., "Quality of life: a valid and reliable measure of therapeutic efficacy in the treatment of inflammatory bowel disease. Canadian Crohn's Relapse Prevention Trial Study Group," *Gastroenterology* 106(2), 287-96 (1994); Brazier, et al., "Validating the SF-36 health survey questionnaire: new outcome measure for primary care," *BMJ* 305(6846), 160-04 (1992).

The safety and toxicity of LDN were assessed by adverse events, laboratory parameters, and vital signs. Nonhematologic and hematologic toxicity were determined by the WHO criteria. See, Oken, et al., "Toxicity and response criteria of the Eastern Cooperative Oncology Group," *Am. J. Clin. Oncol.* 5(6), 649-55 (1982).

An intent-to-treat analysis was performed in which the available data from all evaluable patients were included in the statistical analysis. The parameters of measurement (CDAI scores, laboratory values, and quality of life surveys) were analyzed by a biostatistician comparing baseline values to those obtained monthly and four weeks post-therapy. A longitudinal data analysis based upon the linear mixed-effects model was applied using PROC MIXED program (available from SAS Institute Inc., Cary, N.C.). The Bonferroni statistical method was used to adjust significance where analysis including multiple comparisons to the baseline were made. P-values for binary outcomes response and remission were calculated using the exact test for binomial proportions.

The characteristics of the patients at enrollment are shown in Table 1, including age, gender, and body weight. Most patients had both small bowel and colonic disease, and two patients had active perianal fistulas. Eight patients had prior surgical resection performed for their Crohn's disease. Seventy-six percent of patients had prior treatment with anti-TNF-α therapy and were either allergic, intolerant, or unresponsive to this medication. Concomitant medications for Crohn's disease taken by patients throughout the study are also shown in Table 1 hereinabove.

Statistical analysis showed that there was no significant change in body weight from screening visit through week 16 of the study (data not shown). Two patients elected to discontinue taking routine medications for Crohn's disease prior to week 12 and symptoms of Crohn's disease recurred in one of them. Data from both patients were analyzed with an intent-to-treat paradigm. The two subjects with entercutaneous and rectovaginal fistulas had closure of the fistulas with LDN therapy.

Figure 2:
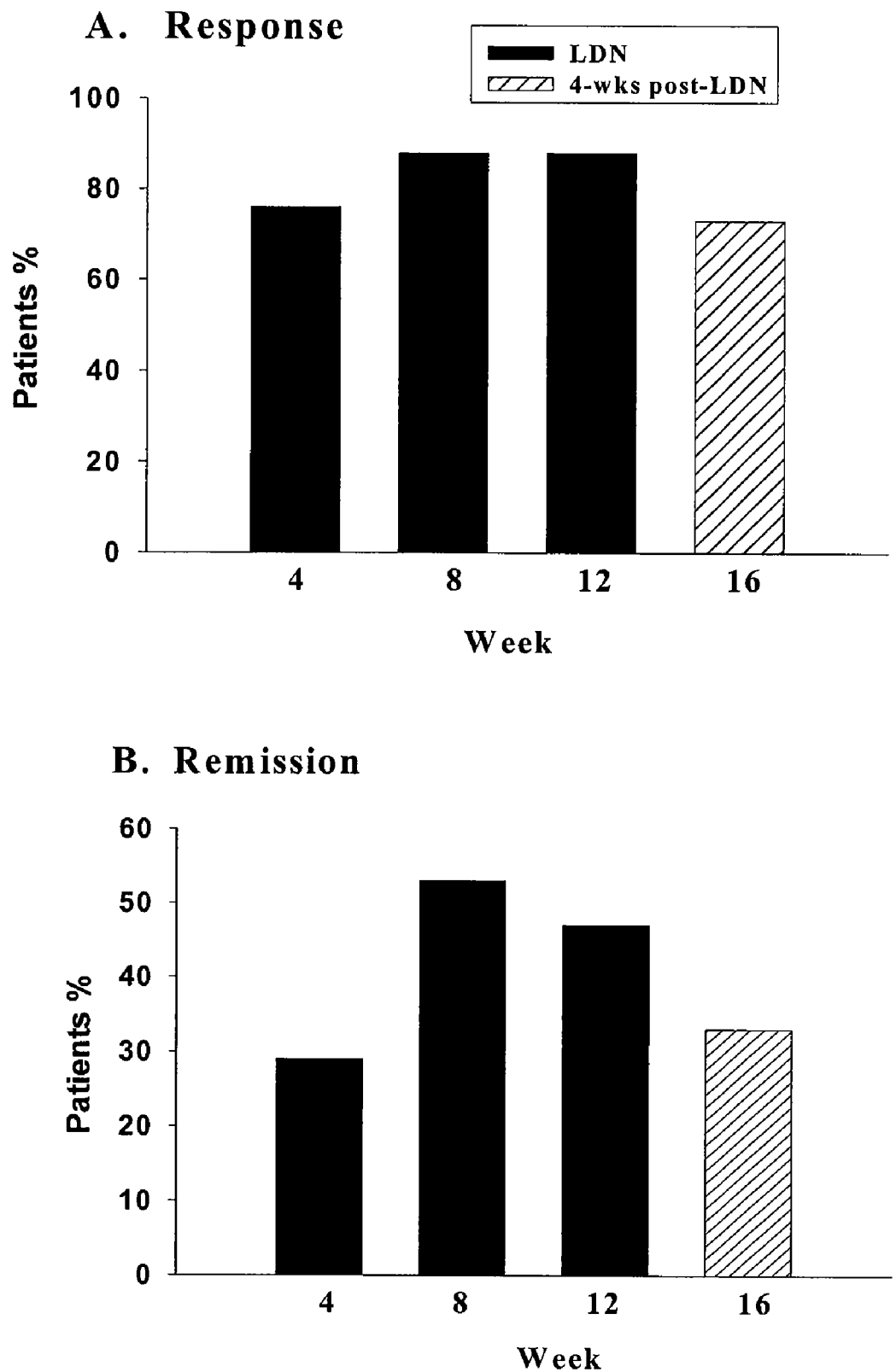
FIG. 2 illustrates the percent of patients responding, and the percent of patients achieving remission, to LDN therapy.
Figure 3:
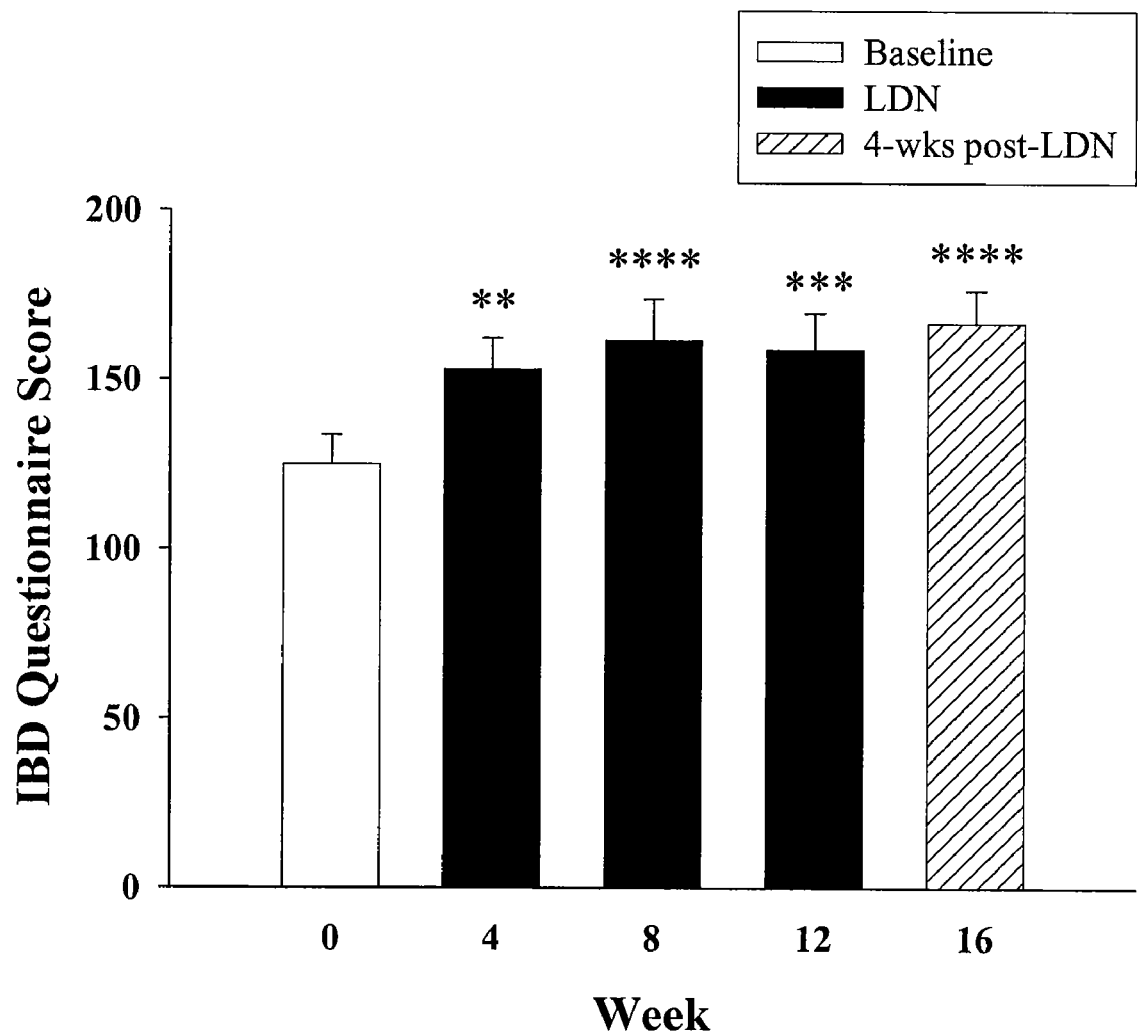
FIG. 3 illustrates mean Inflammatory Bowel Disease Questionnaire scores±SEM associated with LDN therapy in human patients.
Figure 4:
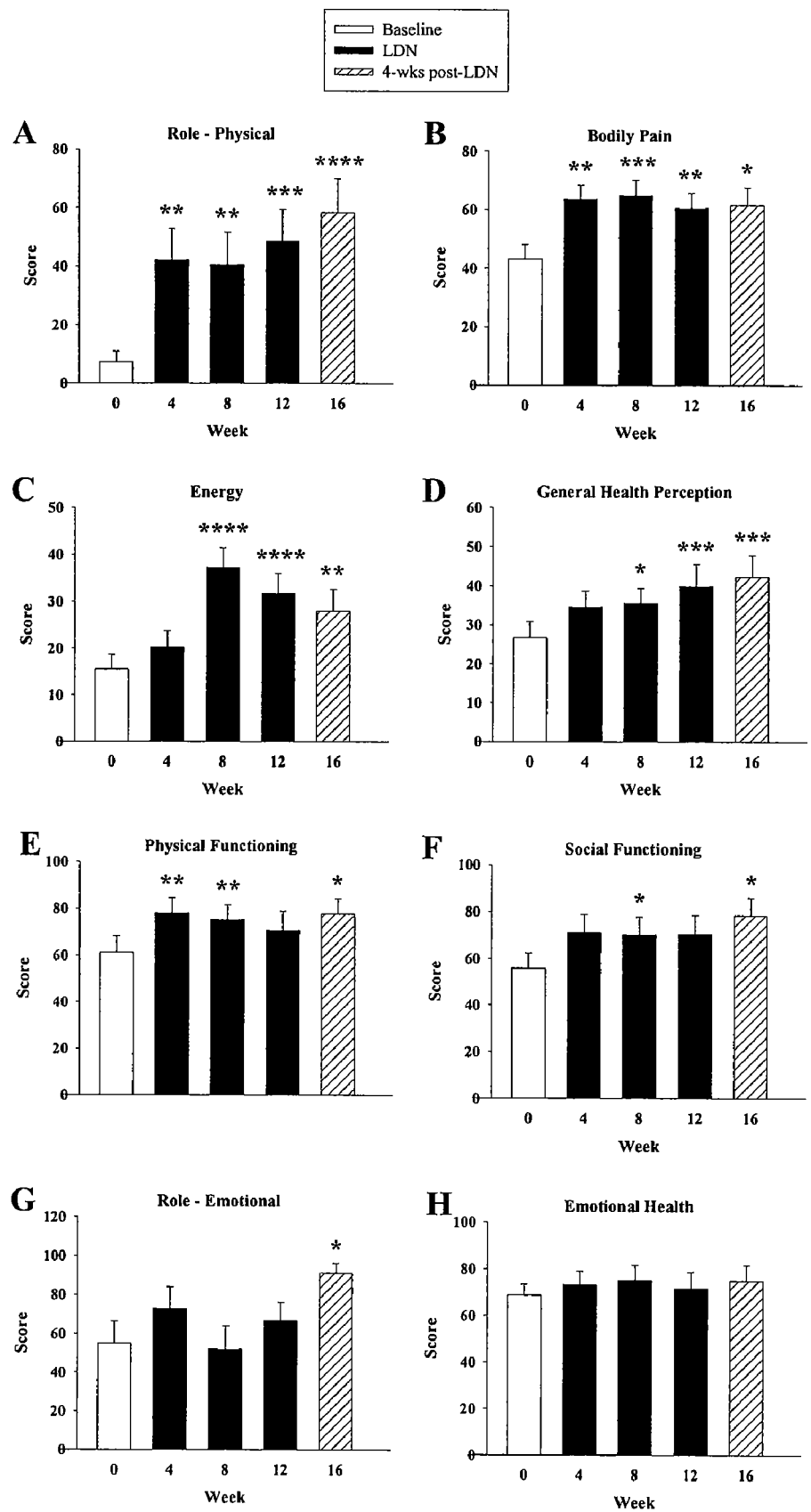
FIG. 4 illustrates mean SF-36 Health Survey scores±SEM associated with LDN therapy in human patients.

Referring to the drawings, FIG. 1 illustrates the mean Crohn's Disease Activity Index (CDAI) scores±SEM, shown at baseline (week 0), weeks 4, 8, and 12 after initiation of LDN therapy and 4 weeks after discontinuation of LDN therapy (week 16). **=Significantly different from baseline at $p<0.0001$. FIG. 2 shows the percent of patients responding (FIG. 2A), and the percent of patients achieving remission (FIG. 2B), to LDN therapy, shown at weeks 4, 8, and 12 and 4 weeks after discontinuation of LDN therapy (week 16). FIG. 3 illustrates mean Inflammatory Bowel Disease Questionnaire (IBDQ) scores±SEM, shown at baseline (week 0), weeks 4, 8, and 12 after initiation of LDN therapy, and 4 weeks after discontinuation of treatment (week 16). Significant differences from baseline are shown as $p<0.01$, *$p<0.001$, and **$p<0.0001$. In FIG. 4, mean SF-36 Health Survey scores±SEM are shown at baseline (week 0), weeks 4, 8, 12 of LDN therapy, and 4 weeks after discontinuation of treatment (week 16) for each of the parameters measured by the SF-36 Health Survey. Significant differences from baseline values included the following: *$p<0.05$, $p<0.01$, *$p<0.001$, and ****$p<0.0001$.

CDAI scores were used to measure the patient's disease activity and inflammatory response to LDN therapy. Mean CDAI scores (FIG. 1) at weeks 4, 8, and 12 following the initiation of LDN therapy were 41%, 55% and 49%, respectively decreased from baseline. Four weeks after discontinuation of therapy (week 16), the mean CDAI score was 45% less than baseline and not statistically different from the mean scores measured during the therapy. FIG. 2 shows the percentage of patients responding to therapy (FIG. 2A), as well as the percentage of subjects achieving a remission of disease (FIG. 2B). At one month after treatment, 76% had achieved a response to therapy (a decrease in the CDAI score by 70 points), and at 8 and 12 weeks, 88% showed a response. Four weeks after discontinuation of LDN, 73% continued to show a response. At one month after starting LDN therapy, 29% of the patients had achieved a remission (a CDAI score of 150 points or less), and at weeks 8 and 12 of LDN therapy, 53% and 47%, respectively, had achieved remission (FIG. 2B). Four weeks after discontinuation of LDN therapy, 33% of the subjects were in clinical remission. Therefore, at some point during the 16-week trial, 89% of patients exhibited a response ($p<0.001$), and of 67% achieved a remission ($p=0.07$) with LDN.

Two standardized quality of life surveys, the Inflammatory Bowel Disease Questionnaire (IBDQ) (FIG. 3) and the SF-36

Health Survey (FIG. 4) were administered to patients receiving LDN treatment. By both measures, patients experienced a significant improvement in their quality of life on LDN therapy. With regard to the IBDQ survey, significant improvement in quality of life was noted compared to baseline at weeks 4, 8, and 12 on LDN, as well as one month after completion of treatment.

Patients experienced a significant improvement in quality of life in a variety of parameters as measured by the SF-36 Health Survey (FIGS. 4A-4H). At weeks 4, 8, and 12 of therapy with LDN resulted in a 5- to 8-fold improvement in physical role scores (FIG. 4A) and a 61-65% improvement in bodily pain (FIG. 4B). Energy scores at weeks 8 and 12 of LDN treatment (FIG. 4C) were at least 2-fold greater than at the time of initiation of therapy, whereas the scores for health perception (FIG. 4D) were 33% and 49%, respectively, greater than baseline. At 4 and 8 weeks of LDN therapy, the physical function (FIG. 4E) was 23% greater than baseline values. Social function (FIG. 4F) was 70% greater than baseline at weeks 4, 8, and 12, but was only statistically different at week 8. Role-emotional (FIG. 4G) and emotional health (FIG. 4H) were comparable to baseline values at weeks 4, 8, and 12 of LDN treatment. At 4 weeks after termination of LDN (i.e., week 16), all parameters except emotional health showed improvement ranging from 27% to an 8-fold improvement over baseline.

At weeks 4, 8, and 12 of LDN therapy there was no change from baseline in CBC or chemistry values. Liver panels were not altered from baseline levels at week 12. Assessment of CBC at week 2 of LDN therapy was comparable to baseline values. C-reactive protein levels decreased from a median value of 2.6 (normal <0.8) at baseline to a value of 0.9 by the $12^{th}$ week of treatment, and this change was statistically significant (p=0.03). The ESR decreased from a mean baseline value of 23.3±0.4 mm/hr to 17.9±0.3 mm/hr, which was also significant (p=0.04). Baseline plasma enkephalin levels were 9.5±2.8 pg/mL, and decreased to a value of 3.6±1.0 pg/mL at week 12 of LDN therapy, but this difference in plasma enkephalin levels was not statistically significant.

The most frequently reported side effect with LDN therapy was sleep disturbances, and this was noted in 7 patients; one reported unusual dreams. Five subjects changed the timing of LDN from the evening to morning due to insomnia. In no instance was a dose reduction necessary for sleep disturbances. Other rarely reported events included nausea (N=1), hair thinning (N=1), blurred vision (N=1), irritability (N=1), mood swings (N=1), and mild disorientation (N=1).

The results of this pilot study are the first to show that LDN therapy significantly decreases symptoms and improves quality of life in patients with active Crohn's disease. Two-thirds of enrolled patients achieved remission at some point during LDN treatment. Another finding in this trial was the fairly rapid onset of effect from LDN in that by four weeks there was significant improvement. Corticosteroids may be effective in decreasing symptoms of Crohn's patients in 7-10 days, but other medications such as the immunomodulators (e.g., azathioprine and 6-mercaptopurine) may take 3-4 months to demonstrate improvement in symptoms. Often symptoms recur within one month after discontinuing corticosteroids or aminosalicylates. However, in the present study continued improvement in CDAI scores and quality of life was reported even four weeks after discontinuing LDN.

Another finding in this pilot study was that LDN improved the quality of life of subjects with active Crohn's disease. The baseline value on the IBDQ was similar to that reported in other clinical trials indicating that our subject group did not differ from those used in other studies. Statistical analysis indicated that for two separate quality of life surveys a significant difference from baseline occurred in those individuals on LDN. Moreover, even one month after discontinuation of LDN therapy, the quality of life remained better in almost all parameters measured for these patients. As of the date of application for patent hereof, a double-blinded placebo-controlled Phase II clinical trial of human subjects has not revealed any serious adverse events.

Treatment with LDN provides advantages over other standard therapy for Crohn's disease. The safety profile of LDN appears to be excellent in this study, with infrequent and minor side effects and no known suppression of immunity or increased risk of secondary infections. Cortiocosteroids have significant long-term risks of weight gain, osteoporosis, cataracts, and glucose intolerance. The immunomodulators methotrexate, azathioprine, 6-mercaptopurine, and cyclosporine all impair immune function increasing the risk for infections and perhaps malignancies. In addition to immunosuppression with the new anti-TNF-α compounds, these drugs can also increase the risk of reactivation of tuberculosis and induce a lupus-like reaction, serum sickness syndrome, or anaphylaxis. Some investigators have suggested that infliximab (an anti-TNF-α compound) or other immunomodulators may increase the risk of malignancies, in particular lymphomas; however, it is unclear whether the risk is due to the disease itself rather than the medication. Higher doses of naltrexone (i.e., 50 mg) used for alcohol and opioid abuse have been reported to elevate liver transaminases. In contrast, the use of LDN herein at 4.5 mg daily did not change liver transaminases during treatment.

Infliximab has become a standard medical therapy for patients with fistulizing disease associated with Crohn's disease. It is of interest that two subjects in our study with enterocutaneous fistulas noted closure with LDN when they had not previously responded to infliximab. Perhaps closures of the fistulas may be related to decreased intestinal secretions or mucosal healing. Perhaps the fistulas closed as a result of decreased number of bowel movements and improved mucosal fluid absorption.

Medical care for IBD is costly. Aminosalicylate therapy can cost several hundred dollars per month, and an infliximab infusion generally exceeds several thousand dollars (not mention of the time away from the workplace for intravenous administration). Naltrexone is a generic medication and the cost is therefore inexpensive. Moreover, effective mesalamine (PENTASA®, a trademark of Ferring B. V. of The Netherlands) therapy may require up to 8-16 tablets per day. Another advantage of LDN is the once-a-day dosing which may improve patient compliance.

Ulcerative Colitis

In the following detailed example embodiment, the opioid antagonist naltrexone is shown to reduce inflammation of the bowel in a chemically-induced mouse model of ulcerative colitis. The dextran sulfate sodium ("DSS") model of experimental colitis in mice is a common pre-clinical model for IBD due to its ease of administration and efficient and reversible induction of symptoms. The addition of DSS to drinking water induces hematochezia, weight loss, intestinal shortening and infiltration of neutrophils, thus serving as a model for human inflammatory bowel diseases. Breakdown of epithelial barrier function in DSS-treated mice leads to an induction of pro-inflammatory cytokines, which are thought to play a central role in disease progression. Cytokines can both suppress apoptosis and drive activation of immune cells that contributes to a chronic state of inflammation. Treatments aimed at reducing this excessive inflammatory response have demonstrated therapeutic promise in DSS models. Therefore, DSS-treated mice are particularly suitable for proof-of-concept studies of novel IBD therapeutics and treatments that may reduce the cytokine-induced inflammatory state. The effect of naltrexone on the progression of DSS-induced colitis in mice was examined. To more accurately model therapeutic invention in established colitis, chemical induction preceded the initiation of treatment. The ability of naltrexone to reverse the acute inflammatory responses induced by DSS was analyzed at the level of whole animal symptoms, tissue histology, and RNA profiling.

Figure 5A:
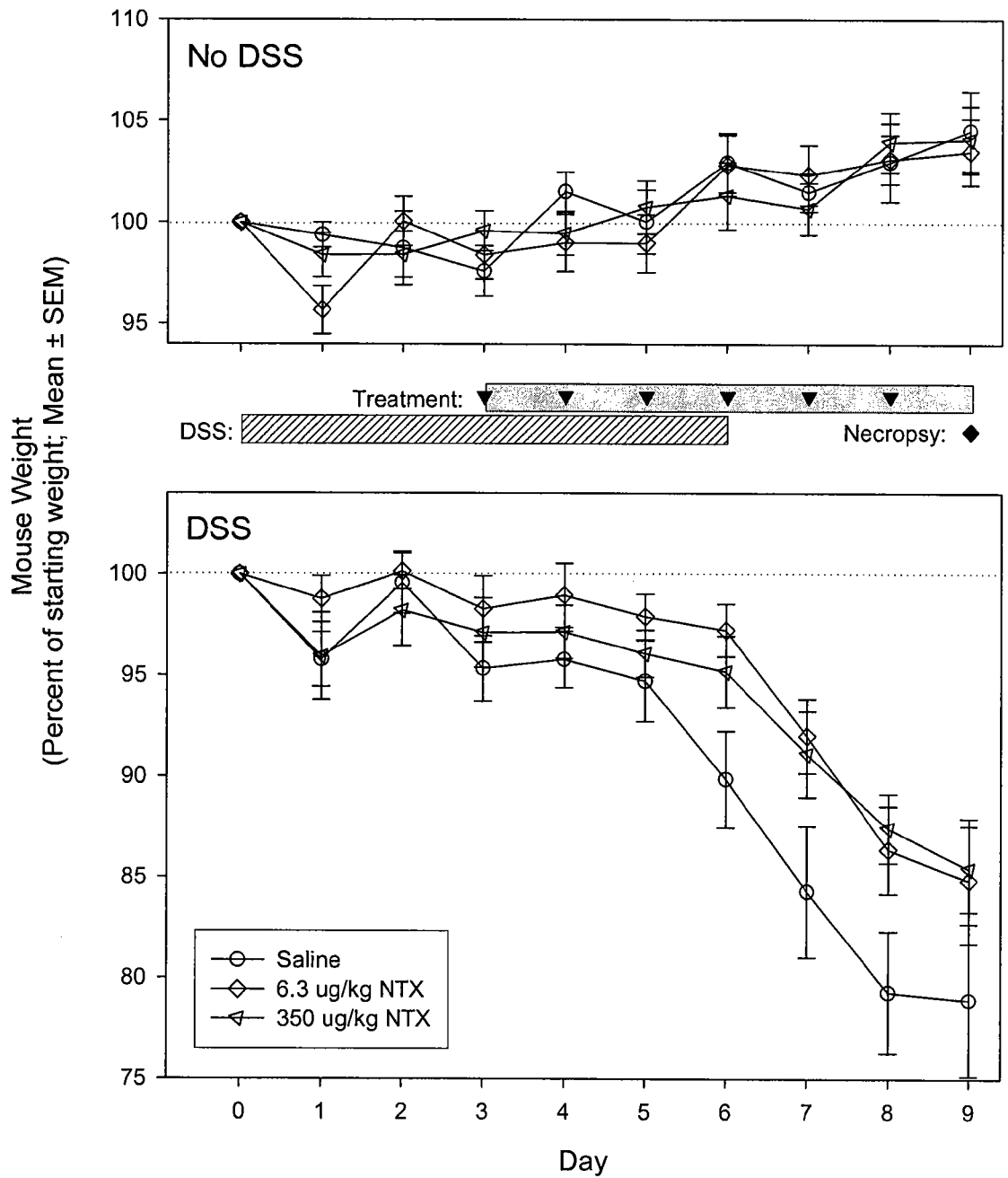
FIG. 5A illustrates the mean weight of laboratory animals receiving either normal drinking water (upper panel) or 2% DSS in drinking water (lower panel).

Six to eight-week-old male C57 black/6J mice (Charles River Laboratories, Inc., Wilmington, Mass.) were randomly allocated into one of two groups of 24 mice each. Food and water were provided ad libitum. The first group (Normal) received normal drinking water and the second group (DSS) received water containing 2% dextran sulfate sodium having a molecular weight of 40,000 (TdB Consultancy AB, Uppsala, Sweden) for six days followed by normal water for three additional days and necropsy on day 9 (FIG. 5A). Each mouse was housed in an individual cage for accurate measurement of food and water intake. Animal weight, water intake, and food consumption were measured daily. Bedding was changed and fresh stool pellets were collected daily and analyzed for occult blood. The colitis disease activity index (DAI) was calculated for each mouse according to the system established by Murthy and colleagues. See, Murthy, et al., "Treatment of dextran sulfate sodium-induced murine colitis by intracolonic cyclosporin," *Dig. Dis. Sci.* 38, 1722-34 (1993). Overt changes in stool consistency were rarely discerned so a modified DAI was calculated based on percent weight loss and stool hemoccult or presence of gross bleeding.

Mice in each group (Normal or DSS) were randomly subdivided into three treatment groups of eight mice each. After 72 hours, mice were treated once daily for six consecutive days with a subcutaneous injection (0.1 mL) of one of the following: saline (control), 6.3 µg/kg naltrexone ("NTX"), or 350 µg/kg NTX (Sigma Chemicals, St. Louis, Mo.). On day 9, all animals were necropsied and their colons resected.

At necropsy, the entire colon was excised, measured in length, and bisected into proximal and distal portions. The proximal and distal colons were additionally divided for RNA extraction and histology. Each histology specimen was fixed in 10% neutral buffered formalin, paraffin embedded and sectioned for hematoxylin and eosin ("H&E") staining. Specimens were examined microscopically and scored based upon the criteria established by Williams et al. by an investigator blinded to the treatment groups. Williams, et al., "Enhanced survival and mucosal repair after dextran sodium sulfate-induced colitis in transgenic mice that overexpress growth hormone," *Gastroenterology* 120, 925-37 (2001). Briefly, a representative longitudinal section from each mouse was scored at six random fields for inflammation severity, extent of inflammation (mucosa, submucosa, transmural) and crypt damage. Each of these scores was weighted to reflect the percent involvement of the overall section and the weighted scores from each of the six fields were averaged to achieve an overall inflammation score for each mouse.

Total RNA was extracted from the distal colon samples (using TRIZOL® available from Invitrogen Corp., Carlsbad, Calif.; TRIZOL® is a trademark of Molecular Research Center, Inc. of Cincinnati, Ohio) and subjected to microarray analysis using a 10K mouse microarray (MWG Biotech, High Point, N.C.) and a Packard Biosciences ScanArray 4000KL machine (Functional Genomics Core Facility of the Section of Research Resources, Penn State College of Medicine). To minimize the impact of variation among animals, RNA from individual mice was pooled within each treatment group. Arrays were run in duplicate and three pairwise comparisons were performed to identify genes for which expression was significantly altered ($p<0.05$) in colitis and by subsequent naltrexone treatment. RNA from Normal+saline, DSS+6.3 µg/kg NTX, and DSS+350 µg/kg NTX were each tested versus DSS+saline. Data were analyzed with GenSpring 6 software (Agilent Technologies, Palo Alto, Calif.).

RNA (18S and 28S bands) was visualized using the Agilent 2100 Bioanalyzer (Agilent Technologies, Santa Clara, Calif.) and concentrations were adjusted. First strand cDNA was then produced from 1.0 µg of total RNA using random hexamer primers and the SuperScript III Reverse Transcription kit (Invitrogen). The concentration and quality of resulting cDNA was quantified and analyzed using the Agilent 2100 Bioanalyzer or spectroscopically with the NanoDrop ND-1000 (NanoDrop Technologies, Wilmington, Del.). Samples were standardized to 30 ng/µL and 60 ng of cDNA per sample was then used as a template for real-time PCR using a SYBR Green Master Mix (Qiagen, Valencia, Calif.). 18S rRNA primers (Eurogentec, San Diego, Calif.) and the following gene-specific primer sequences obtained from PrimerBank (pga.mgh.harvard.edu/primerbank) were used: beta-actin, 6671509a; IL-5, 6754336a; IL-6, 13642311a; IL-12, 6680395a; STAT3, 13277852a; STAT4, 6755670a; Muc2, 3452503a2; TFF3, 6755773a1; Palladin, 9828173a1; and TGF-beta BP, 7305243a1. To exclude the possibility of genomic DNA contamination, control reactions with no cDNA template were also performed for each gene-specific primer set. PCR amplification and analysis were performed with the Applied Biosystems Sequence Detection System 7300 using the Relative Quantification (ddCt). Amplification data for the genes of interest were normalized to 18S within each individual reaction. Triplicate reactions were performed and the resultant data from multiple runs were averaged.

Results were calculated as mean±SEM. Statistical comparisons were performed between NTX treatment sub-groups and their corresponding saline control, as well as between the Normal and DSS groups, comparing corresponding treatments. Parametric analyses were performed (Minitab 13, State College, Pa.) using a modified Bonferroni method to correct for multiple comparisons to controls.

Over the nine day course of study, animals given untreated drinking water exhibited steady weight gain (FIG. 5A, upper panel) while DSS mice showed weight loss beginning between days 4 and 6 (FIG. 5A, lower panel). Steady weight loss continued in the DSS mice until necropsy (day 9). With naltrexone treatment, the weight loss tended to be less compared to DSS+saline; however, the DSS+6.3 µg/kg NTX mice only reached statistical significance on day 6 ($p=0.02$). Among the three DSS sub-groups, no significant difference in weight was evident at necropsy, when the animals had been off DSS for three days.

Figure 5B:
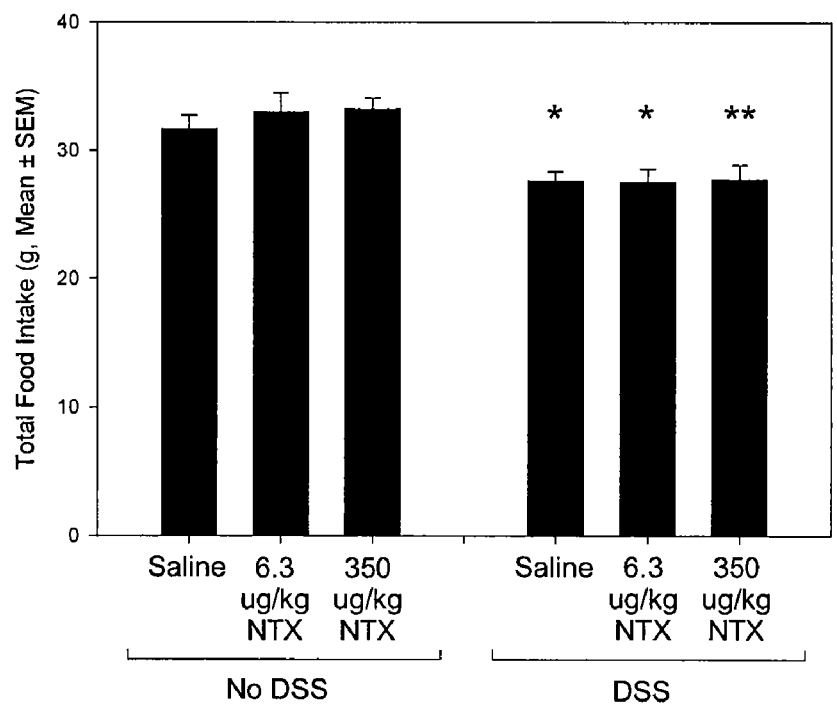
FIG. 5B illustrates the total food intake per animal during the DSS/NTX experiment.
Figure 5C:
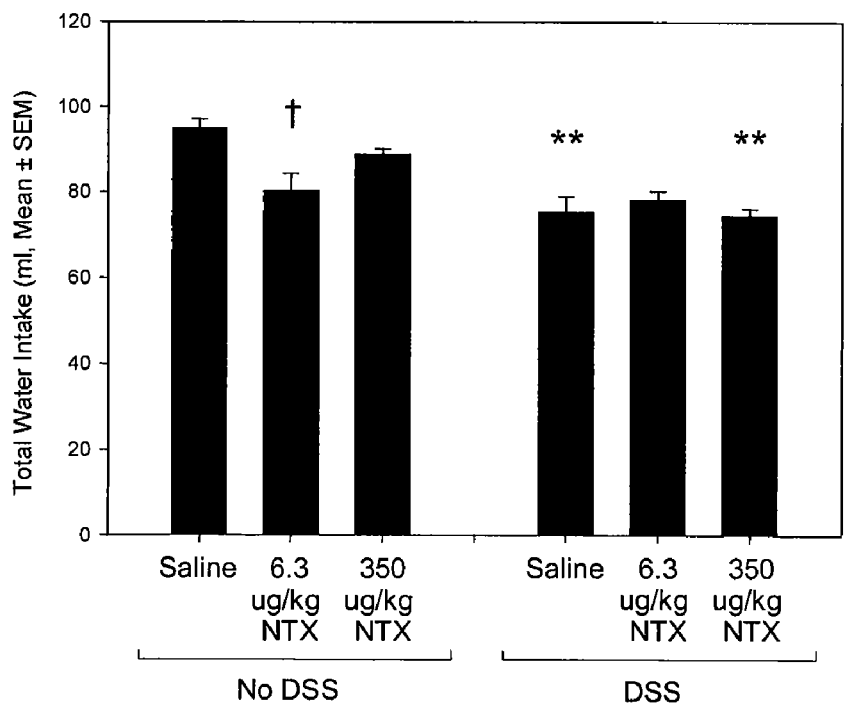
FIG. 5C illustrates the total water intake per animal over the course of the study.

Naltrexone treatment alone had no effect on food consumption (FIG. 5B). However, DSS mice, with or without NTX treatment, had significantly decreased total food consumption (FIGS. 5B and 5C). Total water intake was also reduced in DSS mice compared to mice receiving normal water. Among the Normal mice, a reduction in water consumption was noted in those treated with 6.3 µg/kg NTX relative to saline (FIG. 5C). In FIGS. 5B and 5C, asterisks indicate significantly different values between corresponding DSS and Normal (no DSS) treatment groups (*$p<0.025$; **$p<0.005$; n=7-8). Significant differences between saline- and NTX-treated mice are indicated by a †($p<0.025$).

Figure 6:
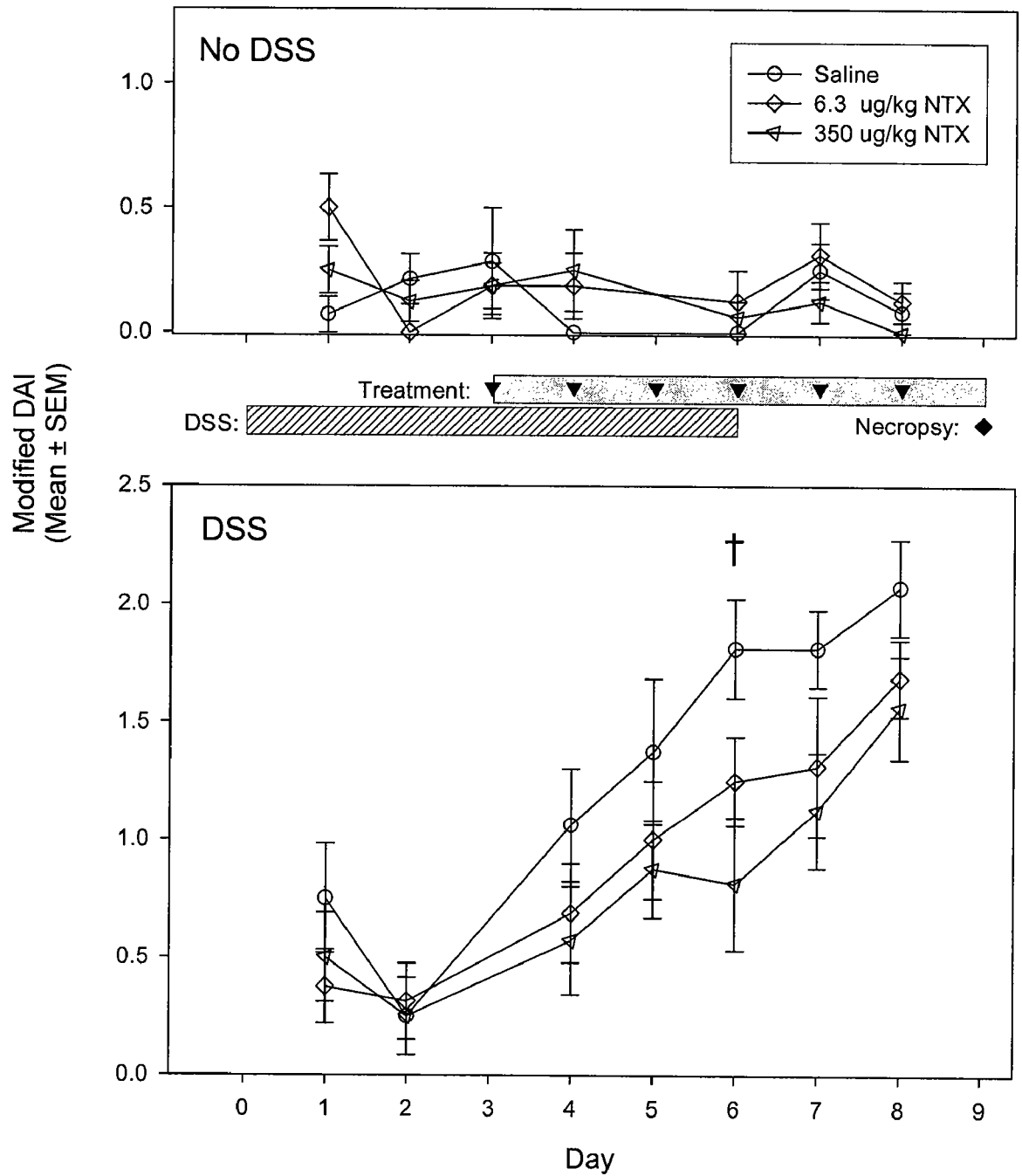
FIG. 6 illustrates the reduction of daily modified Disease Activity Index scores in laboratory animals treated with naltrexone.

To monitor disease progression, a disease activity index ("DAI") was assessed daily for each mouse. Modified DAI scores for all Normal mice (both saline and NTX-treated) showed no evidence of colitis (FIG. 6, upper panel). As with weight loss, the DSS mice developed colitis symptoms, including hemoccult-positive stools and increased DAI scores, by day 4 which continued to increase through day 8 (FIG. 6, lower panel). A reduction in these DAI scores was evident with naltrexone treatment. On day 6, DSS+350 µg/kg NTX animals had significantly lower (55%) DAI scores than DSS+saline mice (p=0.015). In FIG. 6, a significant difference between DSS+350 µg/kg NTX-treated mice and the corresponding DSS+saline group is indicated (†p<0.05; n=7-8).

Reduced colon length, another indicator of DSS-induced colitis, was also evident in all DSS animals (Normal+saline: 9.32±0.39 cm, mean±SEM; DSS+saline: 6.95±0.43; p=0.002). DSS-mice treated with naltrexone had more normal colon lengths, although they were still shorter than in the untreated animals.

Figure 7A:
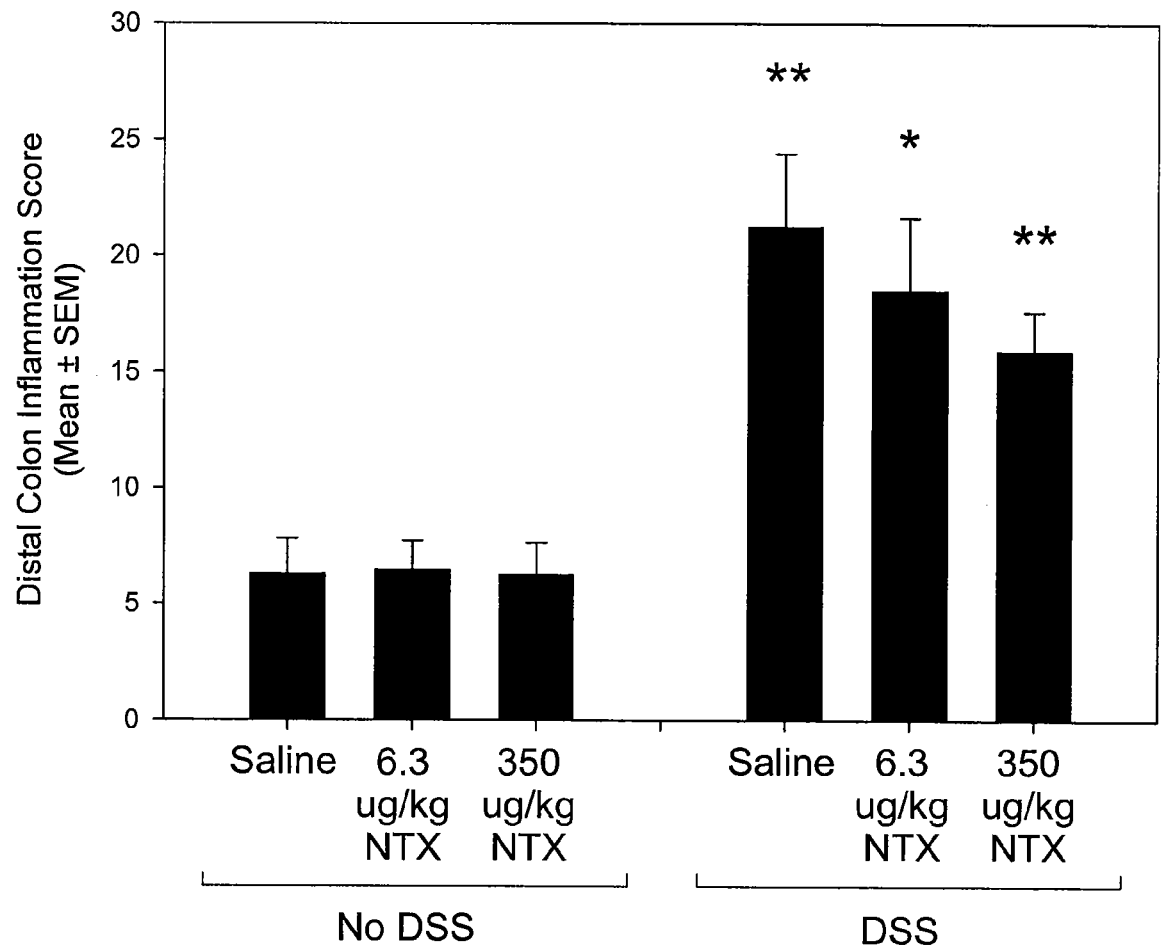
FIG. 7A illustrates the difference in the inflammation of longitudinal sections of the distal colon upon staining and evaluation.
Figure 7B:
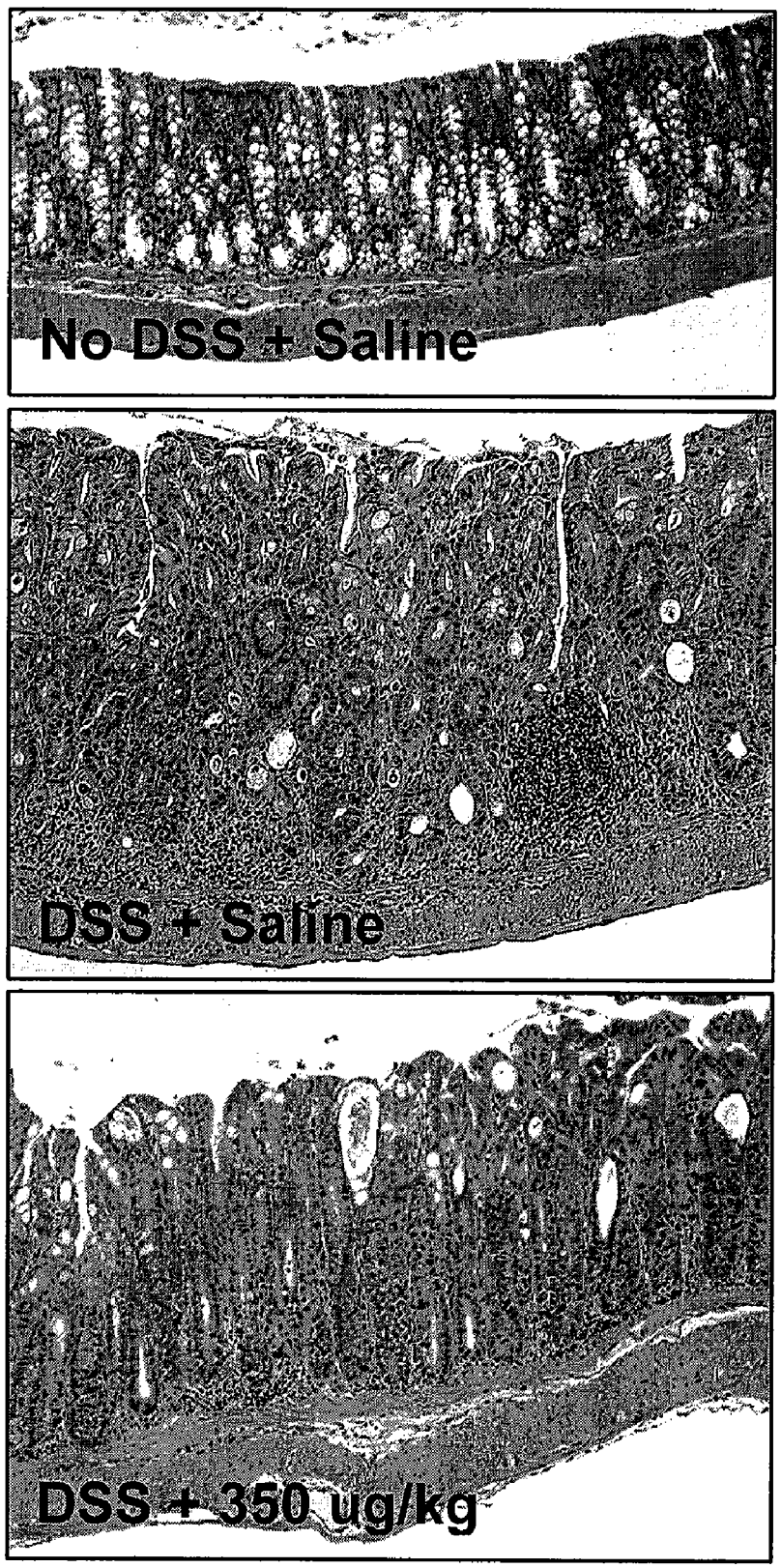
FIG. 7B illustrates representative stained sections of distal colon.

Histological inflammation scores of the distal colon confirm that DSS induced an inflammatory state (FIG. 7A). No differences in colonic inflammation in Normal+saline and Normal±NTX animals were evident histologically. This indicates that naltrexone alone did not alter the mucosal integrity of the colon. All DSS animals had increased inflammation scores, and exhibited crypt damage and increased leukocyte infiltration (FIG. 7B). However, the DSS+NTX animals had a dose-dependent decrease in inflammation and damage, as evidenced by lower inflammation scores in comparison to animals given DSS+saline (FIG. 7A). In FIG. 7A, asterisks indicate significantly different values between corresponding DSS and Normal (No DSS) treatment groups (*p<0.025; **p<0.005; n=7-8). While this trend did not reach statistical significance, the DSS+350 µg/kg NTX mice had improved crypt architecture and fewer invading leukocytes than were observed in the DSS+saline mice (FIG. 7B). In FIG. 7B, representative H&E sections of distal colon are shown. Compared to the normal appearance of healthy murine colon (no DSS+saline; top), leukocyte infiltration and an absence of normal crypt architecture are evident in the DSS+saline mice (middle). Improved architecture and less inflammation are clearly discernable in DSS mice treated with 350 µg/kg naltrexone (bottom of FIG. 7B).

Differences in distal colon gene expression between Normal+saline, DSS+saline, and DSS+NTX mice were initially assessed using a murine spotted oligonucleotide array. Out of 9800 genes on the arrays, 506 genes were initially identified as being significantly changed (p<0.05) in DSS+saline mice when compared to Normal+saline mice (data not shown). Among the most differentially expressed genes were mucin (Muc2), trefoil factor (TFF3), and TGF-beta binding protein. Naltrexone treatment (either 6.3 or 350 µg/kg) restored the levels of these mRNAs in DSS animals to varying extents. However, upon subsequent validation by quantitative RT-PCR, the levels of these three mRNAs in DSS+saline and DSS+NTX animals were not significantly different from Normal animals.

Because naltrexone reduced the inflammatory histology of DSS-induced colitis, the expression of several genes of interest, including both cytokines and downstream mediators, was examined by real-time RT-PCR. Expression of beta-actin, cytokines IL-5, IL-6, IL-12 and transcription factors STAT3 and STAT4, were assessed using 18S rRNA as an endogenous control. The expression of beta-actin and IL-5 were not significantly changed by either DSS+saline or by DSS+NTX (FIG. 8A). By contrast, cytokines IL-6 and IL-12, known to be up-regulated in DSS-induced colitis, were increased in DSS+saline animals in comparison to Normal controls (FIGS. 8B and 8C). The increase in IL-6 mRNA was 73-fold, while the significant increase in IL-12 was more modest (three-fold). Upon treatment with naltrexone, levels of IL-6 and IL-12 were greatly reduced in DSS mice. For IL-12, naltrexone treatment restored mRNA expression to that seen in the colitis-free, Normal mice. The reduction in IL-6 was also significant, although levels were not completely restored to those seen in the colitis-free animals.

To assess whether the alteration in the expression of pro-inflammatory cytokines IL-6 and IL-12 mRNAs had functional consequences, the mRNA for downstream signaling intermediates was also measured by real-time RT-PCR. Both STAT3, downstream of IL-6, and STAT4, downstream of IL-12, were increased in DSS+saline animals (2.20-fold and 8.03-fold, respectively), again indicating a pro-inflammatory response had been induced (FIGS. 8B and 8C). However, both STAT3 and STAT4 mRNA levels were decreased by greater than 50% after naltrexone treatment. In fact, levels of STAT3 mRNA in the naltrexone-treated animals were statistically indistinguishable from colitis-free, Normal controls. Although STAT4 mRNA levels were significantly reduced by naltrexone treatment, they were still slightly higher than in the Normal mice.

Figure 8:
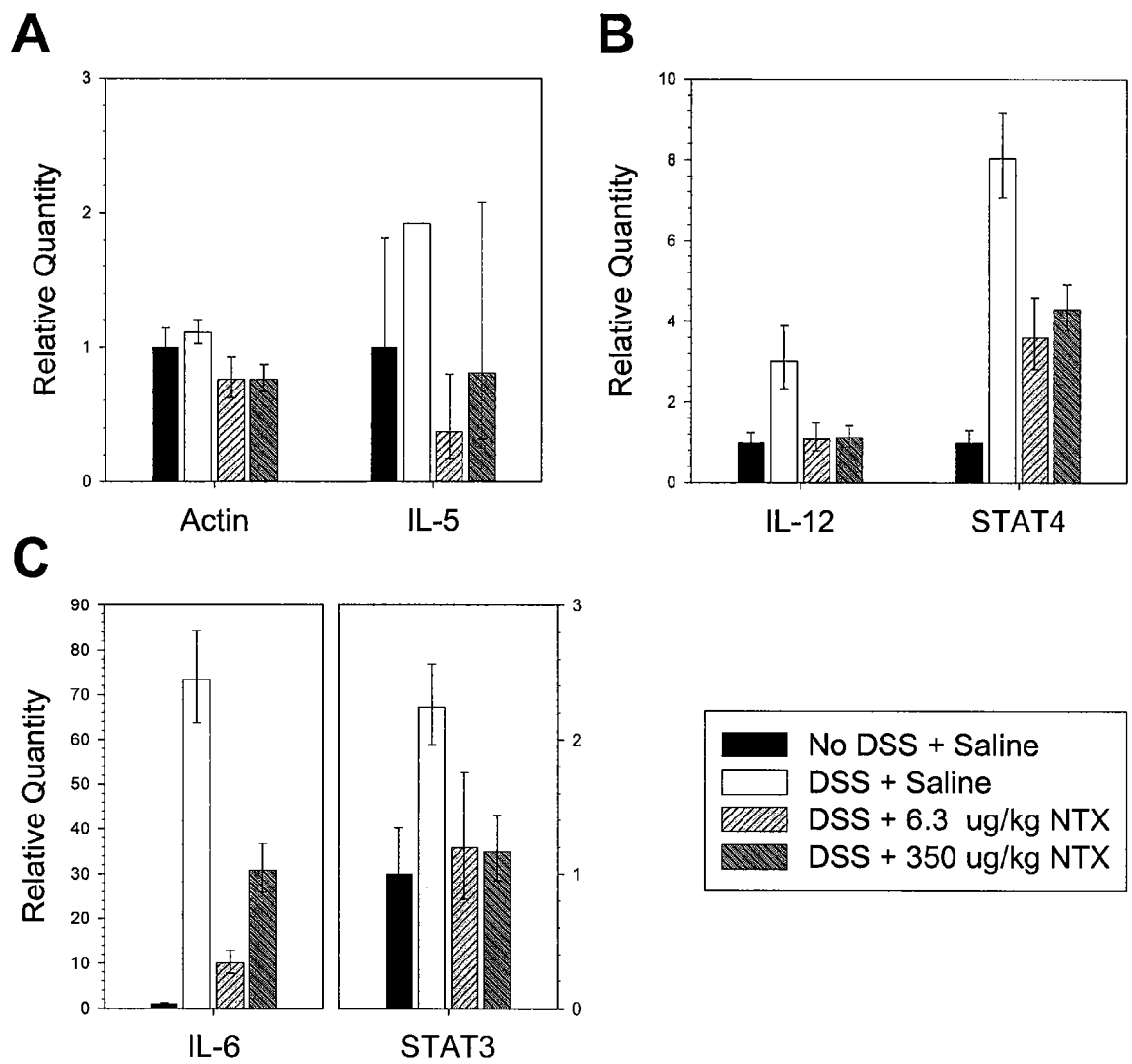
FIG. 8 illustrates the real-time RT-PCR quantification of total RNA from the distal colons of control mice, mice with untreated colitis, and mice with colitis treated with naltrexone.

In FIG. 8, histogram columns represent the relative quantity (RQ=2−DDCT) for each calibrator/target pair. Bars represent a 95% confidence interval (CI) around the relative quantity, and significance is based on non-overlapping CIs. Relative RNA levels for (A) beta-actin and the cytokine IL-5; (B) cytokine IL-12 and its downstream effector STAT4; and (C) cytokine IL-6 and its downstream effector STAT3, reveal significant DSS-induced elevations in pro-inflammatory mediators, and significant restoration toward normal levels when animals were treated with naltrexone.

This study is the first to report improvement of colitis in a murine model upon treatment with an opioid antagonist. Naltrexone treatment resulted in a rapid mitigation of colitis symptoms in DSS mice, while in the absence of colitis, it had no significant impact. DSS was administered for three days prior to either saline or naltrexone injections, emulating a condition of established bowel inflammation preceding treatment. Animals with DSS in their drinking water exhibited significant weight loss and symptoms of colitis; however, within three days of treatment with 350 µg/kg naltrexone, both weight loss and disease symptoms were decreased. Inflammation was also improved as indicated by histology at the study's conclusion. Indeed, the differences in the histological inflammation scores may have been more pronounced if evaluated at an earlier time point while DSS was still being administered. Cessation of DSS on day 6 may have conceivably allowed for partial recovery, mollifying potentially greater significance of the naltrexone treatment.

A robust, pro-inflammatory response characteristic of IBD was further confirmed at the molecular level. Significant elevations in the gene expression of pro-inflammatory cytokines IL-6 and IL-12 were observed with DSS. Molecular evidence also indicated that subsequent naltrexone treatment had a dramatic impact on these pro-inflammatory signaling pathways, significantly decreasing expression of IL-6 and IL-12 in DSS mice to normal or near-normal levels. These decreases in cytokine expression also proved to be functional—reducing the expression of the downstream signaling molecules, STAT3 and STAT4. By moderating the over-stimulation of immune responses and restoring cytokine levels, naltrexone treatment allowed a more normal mucosal structure to reappear. By this means, naltrexone treatment reversed the increase in both the molecular markers of disease and the physiological symptoms of colitis induced by DSS.

Since current therapies, such as anti-TNF-α monoclonal antibodies, are designed to eliminate pro-inflammatory cytokines, these therapies carry an increased risk of infection due to immune suppression. Humanized monoclonal antibodies also show diminished efficacy over time and have significant secondary complications, decreasing their suitability for long-term use. Because naltrexone down-regulates but does not eliminate pro-inflammatory cytokines, naltrexone therapy may have fewer undesirable side-effects than currently used agents. Additionally, the versatility of naltrexone for oral administration presents advantages in patient compliance.

While the invention has been described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to any particular embodiments disclosed as the best mode contemplated for carrying out this invention, but that the invention will include all embodiments falling within the scope of the appended claims.

The invention claimed is:

1. A method for treating a bowel disease comprising administering to a subject in need thereof a therapeutically effective dose less than 50 mg of an opioid antagonist effective to treat a bowel disease in said subject, wherein said bowel disease is characterized by inflammation or ulceration of the intestinal wall and wherein the opioid antagonist is selected from the group consisting of naltrexone, nalmefene, naloxone and pharmaceutically acceptable salts thereof, and combinations thereof.

2. The method according to claim 1, wherein said bowel disease is further characterized by abdominal pain or discomfort, abnormal bowel movement frequency, intestinal stenosis or fistulization, perianal discomfort or pruritis, or abnormal stool consistency.

3. The method according to claim 1, wherein said bowel disease is further characterized by inflammation or ulceration of the small intestine or colon.

4. The method according to claim 1, wherein said bowel disease is further characterized by the presence of a fistula.

5. The method according to claim 1, wherein said bowel disease is inflammatory bowel disease (IBD).

6. The method according to claim 1, wherein said bowel disease is Crohn's disease or ulcerative colitis.

7. The method according to claim 1, wherein said pharmaceutically acceptable salt is a hydrochloride salt thereof.

8. The method according to claim 1, wherein said opioid antagonist is provided as a pharmaceutical composition.

9. The method according to claim 8, wherein said pharmaceutical composition is administered once per day in the evening or at bedtime.

10. The method according to claim 8, wherein said pharmaceutical composition is administered once per day in the morning or after waking from sleep.

11. The method according to claim 8, wherein said pharmaceutical composition is formulated as a solid dosage form suitable for oral administration.

12. The method according to claim 11, wherein said solid dosage form is an immediate release formulation comprising an opioid antagonist and an excipient.

13. The method according to claim 12, wherein said excipient is selected from the group consisting of sucrose, cellulose, and combinations thereof.

14. The method according to claim 8, wherein said pharmaceutical composition is formulated as a topical dosage form suitable for topical administration.

15. The method according to claim 8, wherein said pharmaceutical composition of a therapeutically effective dose less than 50 mg is formulated as a liquid dosage form suitable for oral administration.

16. The method according to claim 8, wherein said liquid dosage form comprises an opioid antagonist and a liquid carrier.

17. The method according to claim 8, wherein said liquid carrier comprises water.

18. The method according to claim 1, wherein said therapeutically effective dose less than 50 mg is from about 1.75 mg to about 4.5 mg of said opioid antagonist.

19. The method according to claim 1, wherein said therapeutically effective dose less than 50 mg is from about 1.75 mg to about 3 mg of said opioid antagonist.

20. A method of pharmaceutical treatment comprising orally administering to a human subject having Crohn's disease or ulcerative colitis a therapeutic pharmaceutical composition once per day in the evening or at bedtime, wherein said pharmaceutical composition comprises from about 3 mg to about 4.5 mg of naltrexone, nalmefene, naloxone, or a hydrochloride salt thereof in an immediate release solid dosage formulation.

* * * * *